(12) United States Patent
Kondo et al.

(10) Patent No.: US 8,381,907 B2
(45) Date of Patent: *Feb. 26, 2013

(54) INDIVIDUAL PACKAGE

(75) Inventors: Hideki Kondo, Kagawa (JP); Masashi Hosokawa, Kagawa (JP); Hitoshi Watanabe, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 146 days.

This patent is subject to a terminal disclaimer.

(21) Appl. No.: 12/595,169

(22) PCT Filed: Apr. 8, 2008

(86) PCT No.: PCT/JP2008/056910
§ 371 (c)(1),
(2), (4) Date: Oct. 8, 2009

(87) PCT Pub. No.: WO2008/126832
PCT Pub. Date: Oct. 23, 2008

(65) Prior Publication Data
US 2010/0078348 A1 Apr. 1, 2010

(30) Foreign Application Priority Data
Apr. 10, 2007 (JP) ................................ 2007-103087

(51) Int. Cl.
*B65D 33/00* (2006.01)
*A61F 13/551* (2006.01)

(52) U.S. Cl. .................... 206/440; 206/438; 604/385.02

(58) Field of Classification Search .................. 206/440, 206/438, 484, 210; 604/385.02, 358; 383/200, 383/207, 209, 205; 229/87.03, 87.05
See application file for complete search history.

(56) References Cited

U.S. PATENT DOCUMENTS

| | | | | |
|---|---|---|---|---|
| 3,092,251 A | * | 6/1963 | Jaggers | 206/446 |
| 4,648,513 A | * | 3/1987 | Newman | 383/204 |
| 4,735,316 A | * | 4/1988 | Froidh et al. | 206/438 |
| 4,881,644 A | * | 11/1989 | Norquest et al. | 206/363 |
| 5,133,457 A | * | 7/1992 | Kadel | 206/438 |
| 5,445,454 A | * | 8/1995 | Barkhorn | 383/207 |

(Continued)

FOREIGN PATENT DOCUMENTS

| | | |
|---|---|---|
| DE | 29718278 U1 | 3/1998 |
| EP | 1707497 A1 | 10/2006 |

(Continued)

OTHER PUBLICATIONS

International Search Report from corresponding PCT application No. PCT/JP2008/056910, dated Jul. 15, 2008, 2 pages.

(Continued)

*Primary Examiner* — Steven A. Reynolds
(74) *Attorney, Agent, or Firm* — Brinks Hofer Gilson & Lioine

(57) ABSTRACT

An individual package of sanitary tampon that can be easily opened and can avoid any unintended seal breakage while being carried. The individual package of tampon comprises a vertically long, flat bag body made of a sheet-shaped member and a tampon with applicator individually enclosed in the bag body. The individual package further comprises a seal breaking part with one or more cut portions provided continuously or intermittently along a given direction of the sheet-shaped member and a buffer structure part provided on one side or both sides of the seal breaking part in the seal breaking direction. The buffer structure part has a slack portion formed by slacking the sheet-shaped member.

7 Claims, 13 Drawing Sheets

U.S. PATENT DOCUMENTS

| | | | |
|---|---|---|---|
| 5,743,460 A * | 4/1998 | Capy et al. | 229/87.03 |
| 5,986,165 A * | 11/1999 | Moder et al. | 604/358 |
| 6,276,529 B1 * | 8/2001 | Feehan, Jr. | 206/469 |
| 6,299,607 B1 * | 10/2001 | Osborn et al. | 604/385.02 |
| 6,773,421 B2 * | 8/2004 | Bosselaar et al. | 604/385.02 |
| 6,955,665 B2 * | 10/2005 | Domeier et al. | 604/385.02 |
| 6,994,696 B2 * | 2/2006 | Suga | 604/385.02 |
| 7,101,358 B2 * | 9/2006 | Domeier et al. | 604/385.02 |
| 7,621,106 B2 * | 11/2009 | Tackett et al. | 53/412 |
| 2003/0065300 A1 * | 4/2003 | Suga | 604/385.02 |
| 2003/0220624 A1 * | 11/2003 | Domeier et al. | 604/385.02 |
| 2004/0112779 A1 * | 6/2004 | Arndt | 206/363 |
| 2006/0212015 A1 * | 9/2006 | Peele | 604/385.13 |
| 2007/0151885 A1 * | 7/2007 | Loyd et al. | 206/440 |
| 2007/0156109 A1 * | 7/2007 | Loyd et al. | 604/385.02 |

FOREIGN PATENT DOCUMENTS

| | | |
|---|---|---|
| JP | S52-18128 U | 2/1987 |
| JP | S62-18128 U | 2/1987 |
| JP | 10-101097 | 4/1998 |
| JP | 2004-097251 | 4/2004 |
| JP | 2007-054087 | 3/2007 |
| JP | 2007-282918 | 11/2007 |
| JP | 2008-259583 | 10/2008 |
| JP | 2008628 A1 | 12/2008 |

OTHER PUBLICATIONS

European Search Report from corresponding European application No. 08740013.1 mailed Dec. 27, 2011 (7 pgs).

* cited by examiner

INDIVIDUAL PACKAGE

RELATED APPLICATIONS

The present application is a 35 U.S.C. §371 national stage filing of International Patent Application No. PCT/JP2008/056910, filed Apr. 8, 2008, to which priority is claimed under 35 U.S.C. §120 and through which priority is claimed under 35 U.S.C. §119 to Japanese Priority Patent Application No. 2007-103087, filed Apr. 10, 2007.

TECHNICAL FIELD

The present invention relates to an individual packaging body, and particularly to an individual packaging body in which a tampon with an applicator is individually housed.

BACKGROUND ART

Conventionally, as an absorbent article that is used by inserting into a vaginal cavity of a woman during menstruation, a so-called sanitary tampon including an absorbent core for absorbing body fluid and the like and a removal cord provided in a back end portion thereof is known. Such a sanitary tampon includes one to be inserted into a body using a cylindrical insertion device called an applicator and one to be inserted into a body directly with fingers without the applicator. For example, in a case of the tampon with an applicator, an applicator that houses an absorbent core is inserted to a predetermined position in a vaginal cavity and the absorbent core is pushed out from the applicator, thereby surely inserting the absorbent core deep into the vaginal cavity. This makes many women choose the tampon with an applicator.

Recently, as such a tampon with an applicator, one with improved portability is preferred in order to prepare for changing the tampon away from home and the like. Consequently, for example, a so-called individually-packed tampon with an applicator, in other words a tampon with an applicator that is packed in a bag body in a substantially elongated shape, is widely used (for example, see Japanese Unexamined Utility Model Application Publication No. S62-18128, hereinafter referred to as Patent Document 1).

In an individual packaging body disclosed in Patent Document 1, a tampon with an applicator is packed inside a vertically long bag body obtained by folding a predetermined film in a substantially rectangular shape and joining an overlapped portion thereof, and a perforated line for opening is formed in a circumferential direction of the bag body of the individually-packed tampon with an applicator. As a result, the individually-packed tampon with an applicator has a structure allowing for easy carrying and easy takeoff of the tampon with an applicator since the individual packaging can be opened by opening the bag body from the perforated line.

DISCLOSURE OF THE INVENTION

Problems to be Solved by the Invention

However, the individual packaging body of the sanitary tampon disclosed in Patent Document 1 was easily torn due to the perforated line. Thus, for example, when the sanitary tampon was carried in a bag or in a makeup pouch, the perforated line could be accidentally torn by random external force such as contact and friction with other objects and the like. If the individual packaging body is accidentally torn, dust and bacteria could get thereinto and make the tampon unsanitary. In particular, since sanitary tampons are used by inserting into the body, unsanitary ones could not be used.

The present invention is made in view of the abovementioned problems and aims at providing an individual packaging body for a sanitary tampon that allows easy opening while avoiding accidental opening when carrying.

Means for Solving the Problems

The present inventors have achieved the present invention based on the discovery that, by providing a buffering portion which absorbs force applied to an individual packaging body that packs a tampon with an applicator individually, to the individual packaging body, accidental opening of the individual packaging body can be avoided. More specifically, the present invention provides the following individual packaging body.

In a first aspect of the present invention, an individual packaging body includes: a tearing portion having at least one slit portion that is formed continuously or intermittently in a predetermined direction; and a buffering structure portion formed on at least one side in a tearing direction of the tearing portion that is orthogonal to the predetermined direction, in which a tampon with an applicator is individually packed in a bag body formed to be long and in a case where a predetermined force that moves a part of the individual packaging body in the tearing direction is applied to a predetermined position that is away from the buffering structure portion in the tearing direction, the buffering structure portion inhibits the predetermined force from transferring to the tearing portion.

Here, the predetermined direction is, for example, a width direction of the bag body in a case where the individual packaging body is intended to be torn by separating a part thereof in a longitudinal direction and, for example, a longitudinal direction of the bag body in a case where the individual packaging body is intended to be torn by separating a part thereof in a width direction.

In addition, the predetermined position is any position to a side of an end portion in the tearing direction of the individual packaging body, between the buffering structure portion and the end portion. In other words, the predetermined position is not a position to be arbitrarily defined and includes any position in the abovementioned range.

Furthermore, the predetermined force is a force that moves a part of the sheet-like member at the predetermined position in the tearing direction, for example, a force that is capable of breaking a part of the bag body that is a non-slit portion in the vicinity of slit portions in the tearing portion.

It should be noted that, the slit portion can be slits that are intermittently formed on the bag body or a part of the bag body being formed to be thin-walled intermittently or continuously in the tearing portion. In other words, the slit portion is required to be easy to tear.

According to a second aspect of the present invention, in the individual packaging body as described in the first aspect, the buffering structure portion is formed to be extendable in a direction of the predetermined force.

According to a third aspect of the present invention, in the individual packaging body as described in the first or the second aspect, in a case where the predetermined force is applied to the predetermined position, moving distance of the tearing portion in the tearing direction is smaller than that of the predetermined position in the tearing direction.

According to a fourth aspect of the present invention, in the individual packaging body as described in any one of the first to the third aspects, the buffering structure portion is formed in the vicinity of the tearing portion.

According to a fifth aspect of the present invention, in the individual packaging body as described in any one of the first to the fourth aspects, the buffering structure portion is formed by folding back the sheet-like member continuously so that peak portions and valley portions alternate continuously in the tearing direction.

According to a sixth aspect of the present invention, in the individual packaging body as described in any one of the first to the fifth aspects, the bag body is flat shaped and includes a first face that is a face in a minor axis direction on which the tearing direction and the buffering structure portion are formed and a second face that is on an opposite side thereof, the buffering structure portion includes a slack portion that is formed by slackening the sheet-like member, and the slack portion is disposed along a surface of the bag body so as to cover the tearing portion.

According to a seventh aspect of the present invention, in the individual packaging body according to the sixth aspects, the buffering structure portion includes a first buffering structure portion that is formed on one side in the tearing direction of the tearing portion and a second buffering structure portion that is formed on another side, in which the second buffering structure portion is formed by slackening the sheet-shaped member, thereby forming a second slack portion that is disposed so as to cover the slack portion.

According to an eighth aspect of the present invention, in the individual packaging body as described in the seventh aspect, in at least any one of the slack portion and the another slack portion, a side edge in the width direction of the bag body is joined with the bag body.

According to a ninth aspect of the present invention, in the individual packaging body as described in any one of the first to the eighth aspects, the tearing portion is formed such that the predetermined direction of the tearing portion is in a width direction of the bag body.

According to a tenth aspect of the present invention, in the individual packaging body as described in any one of the first to the eighth aspects, the tearing portion is formed such that the predetermined direction is in a longitudinal direction of the bag body.

According to an eleventh aspect of the present invention, in the individual packaging body as described in any one of the first to the tenth aspects, the bag body includes a guiding element that indicates a position of the tearing portion or the tearing direction.

According to a twelfth aspect of the present invention, in the individual packaging body as described in any one of the first to the eleventh aspects, the buffering structure portion is formed with an extensible portion.

According to a thirteenth aspect of the present invention, in the individual packaging body as described in any one of the first to the twelfth aspects, the tearing portion includes a first slit portion and a second slit portion that is shorter in length in the predetermined direction than the first slit portion, in which the first slit portion is provided in a substantially central portion in the tearing portion and the second slit portion is provided on both sides of the first slit portion.

According to a fourteenth aspect of the present invention, in the individual packaging body as described in any one of the first to the fifth aspects, the buffering structure portion is formed so that a length thereof in a extended state in the tearing direction is at least 130% of the length thereof in a non-extended state in the tearing direction.

Effects of the Invention

According to the present invention, an individual packaging body for a sanitary tampon that allows easy opening while avoiding accidental opening when carrying can be provided.

EXPLANATION OF REFERENCE NUMERALS

Figure 1:
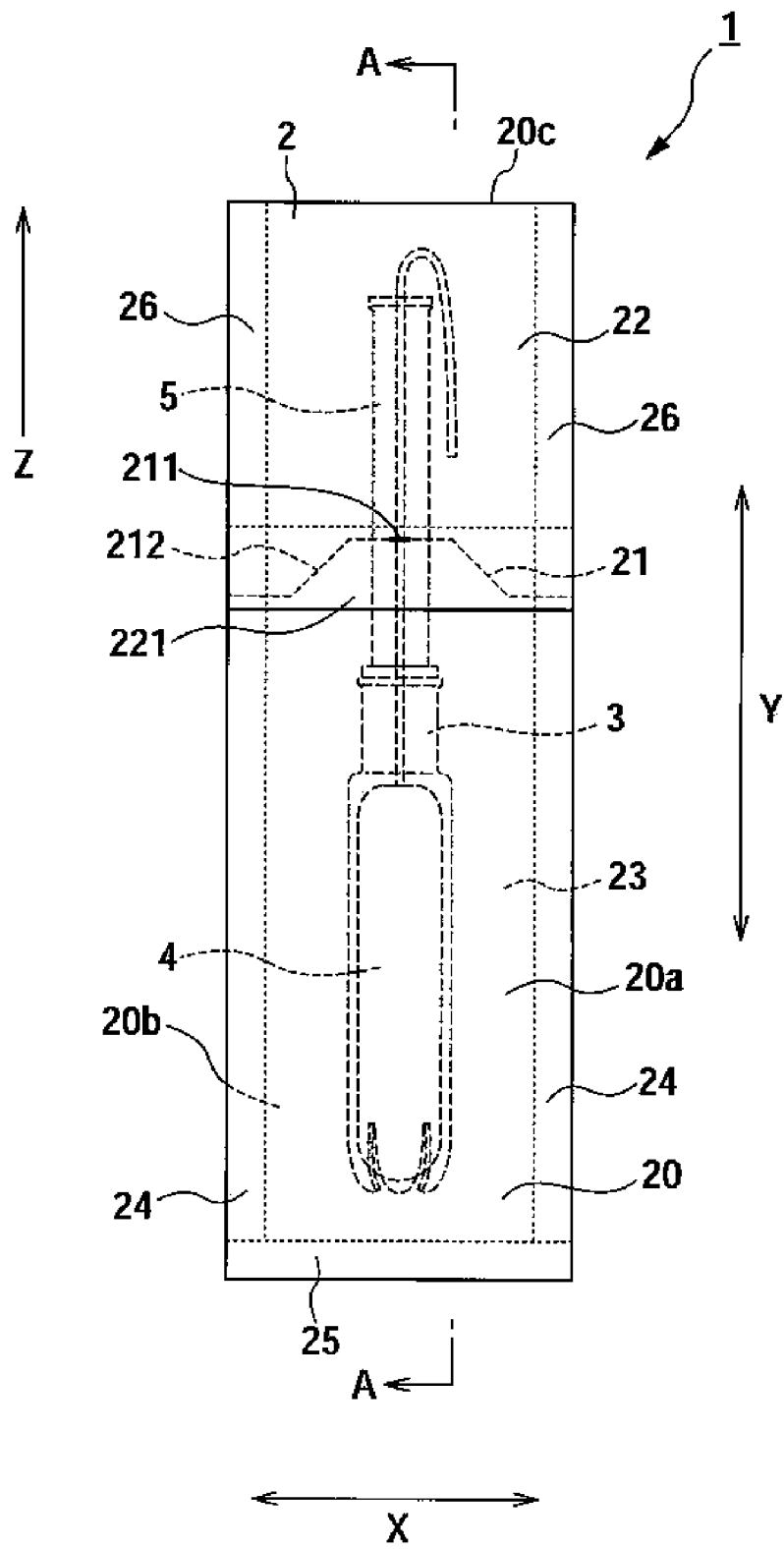
FIG. 1 is a front view of an individual packaging body according to a first embodiment of the present invention.

1 Individual packaging body
2 Bag body
20 Sheet-like member
21 Lid portion
221 Slack portion
221a First slack portion
221b Second slack portion
3 Tampon with an applicator
4 Tampon
41 Absorbent core
42 Removal cord
5 Applicator
51 Outer cylinder
52 Inner cylinder
53 Grip portion

PREFERRED MODE FOR CARRYING OUT THE INVENTION

Embodiments of the present invention are described hereinafter with reference to the drawings. It should be noted that the embodiments of the present invention are not limited to the following examples and the technical scope of the present invention is not limited thereto.

Figure 2:
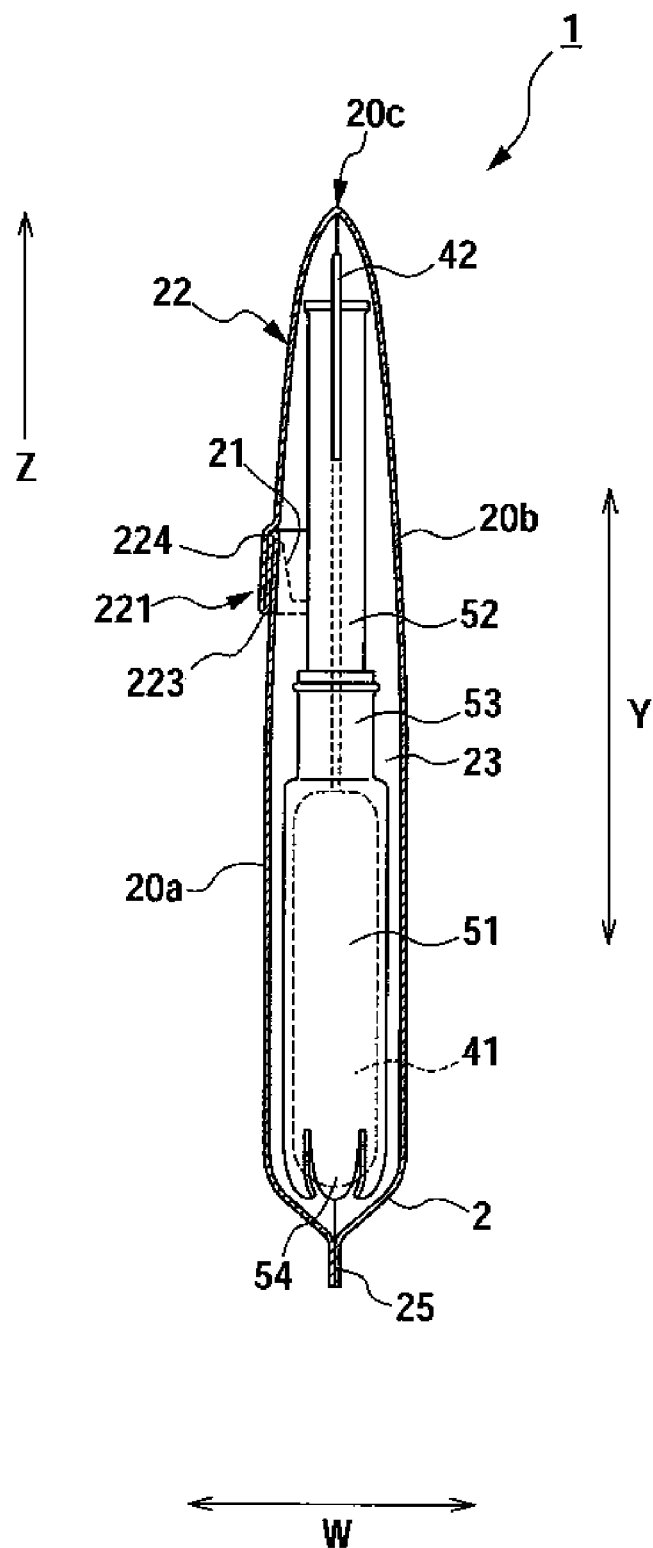
FIG. 2 is a schematic view showing a cross-section taken along line A-A of the individual packaging body shown in FIG. 1.
Figure 3:
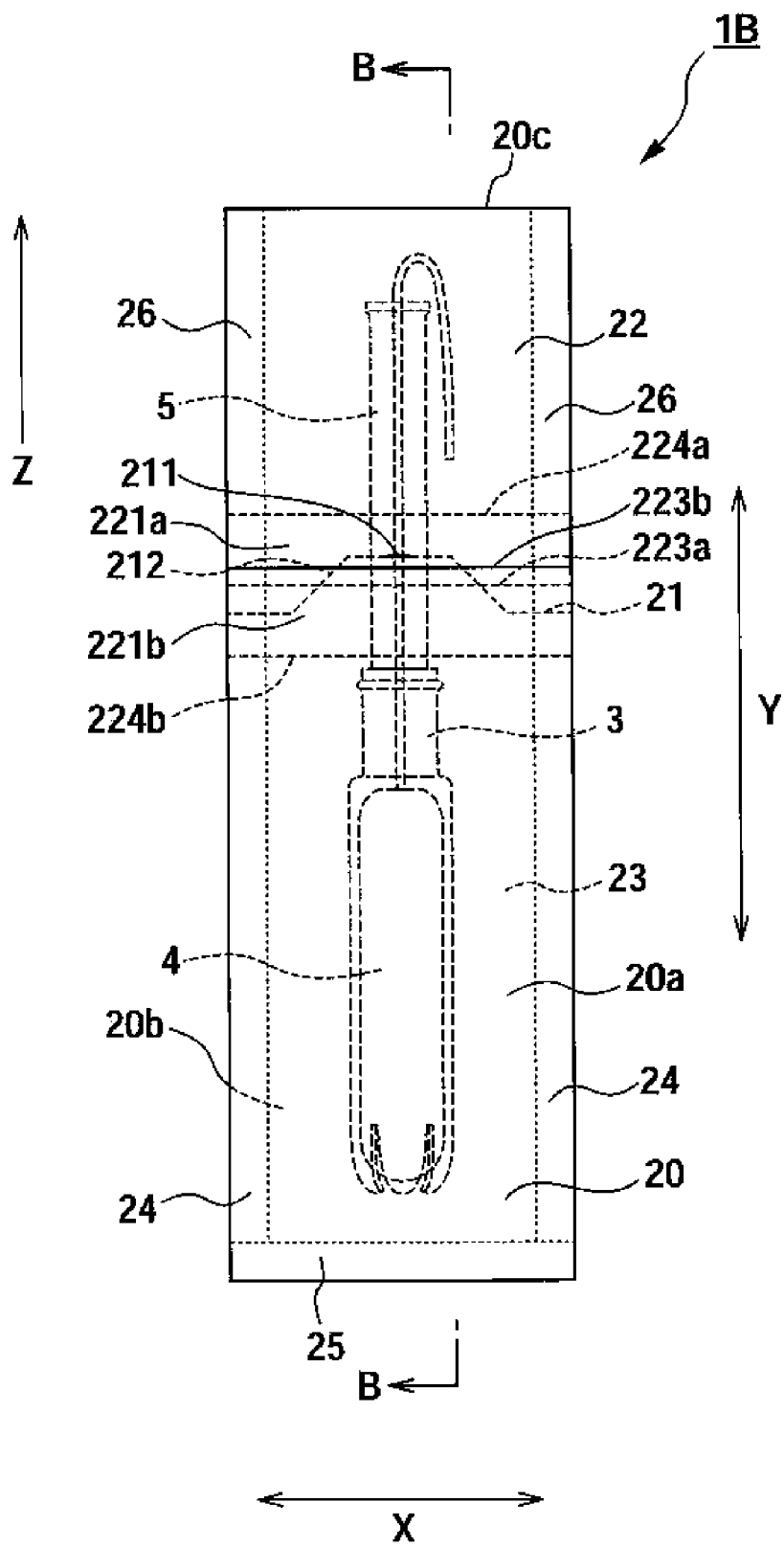
FIG. 3 is a front view of an individual packaging body according to a second embodiment of the present invention.
Figure 4:
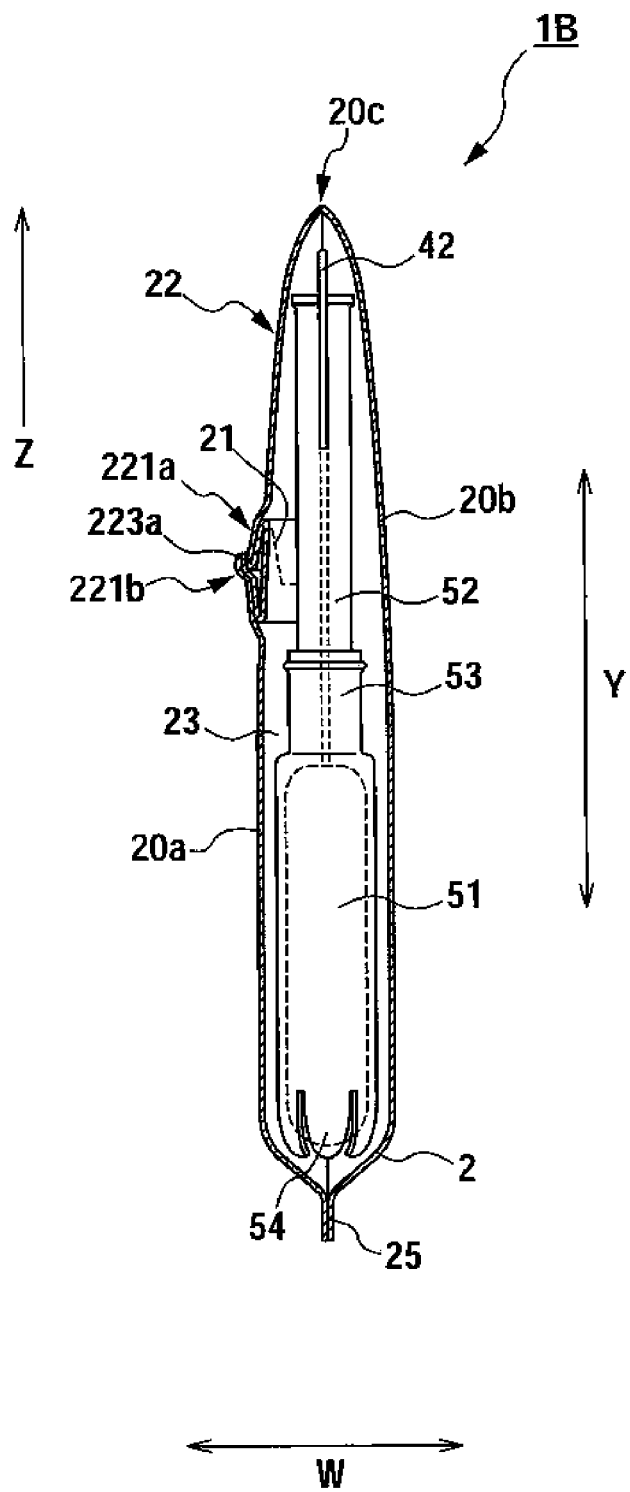
FIG. 4 is a schematic view showing a cross-section taken along line B-B of the individual packaging body shown in FIG. 3.
Figure 5:
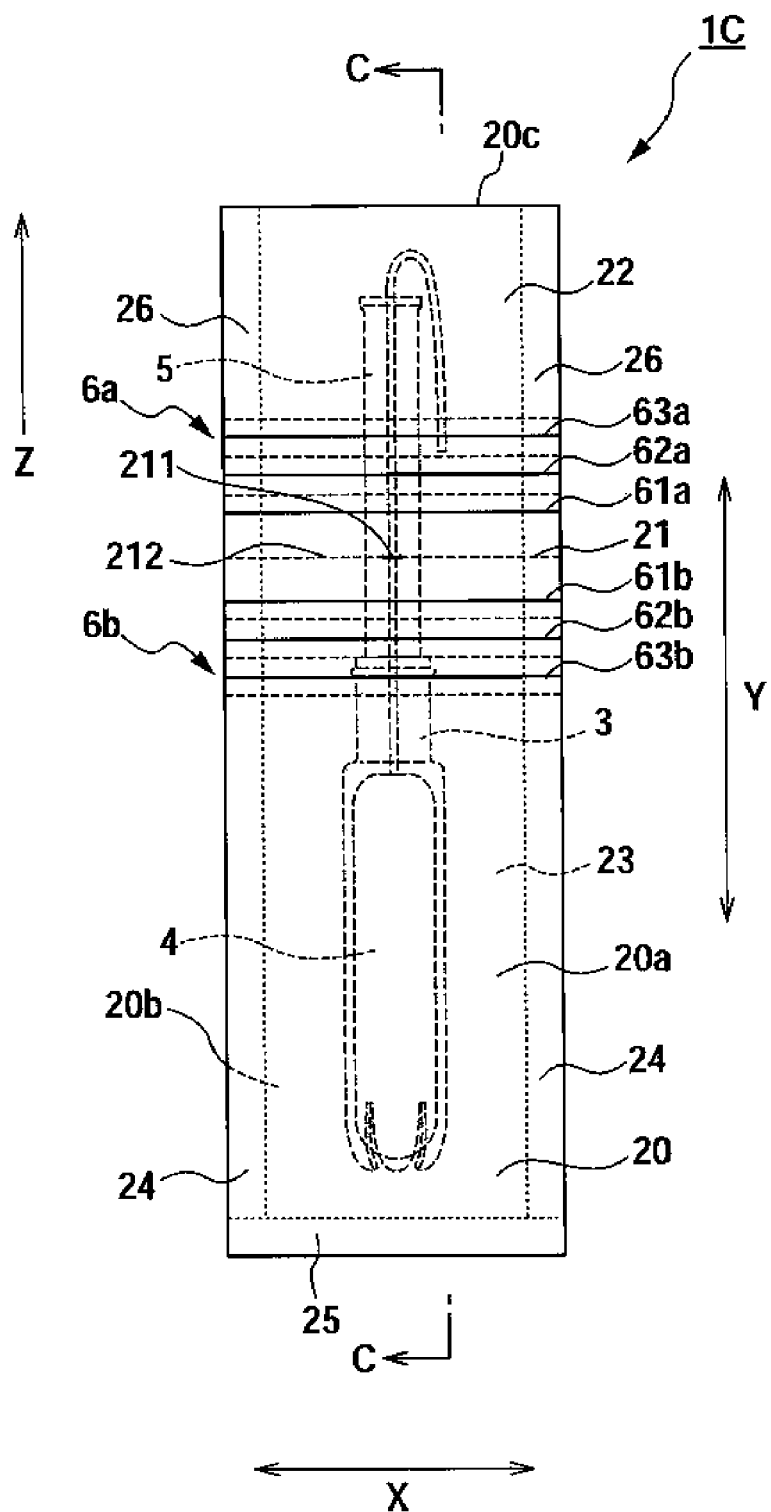
FIG. 5 is a front view of an individual packaging body according to a third embodiment of the present invention.
Figure 6:
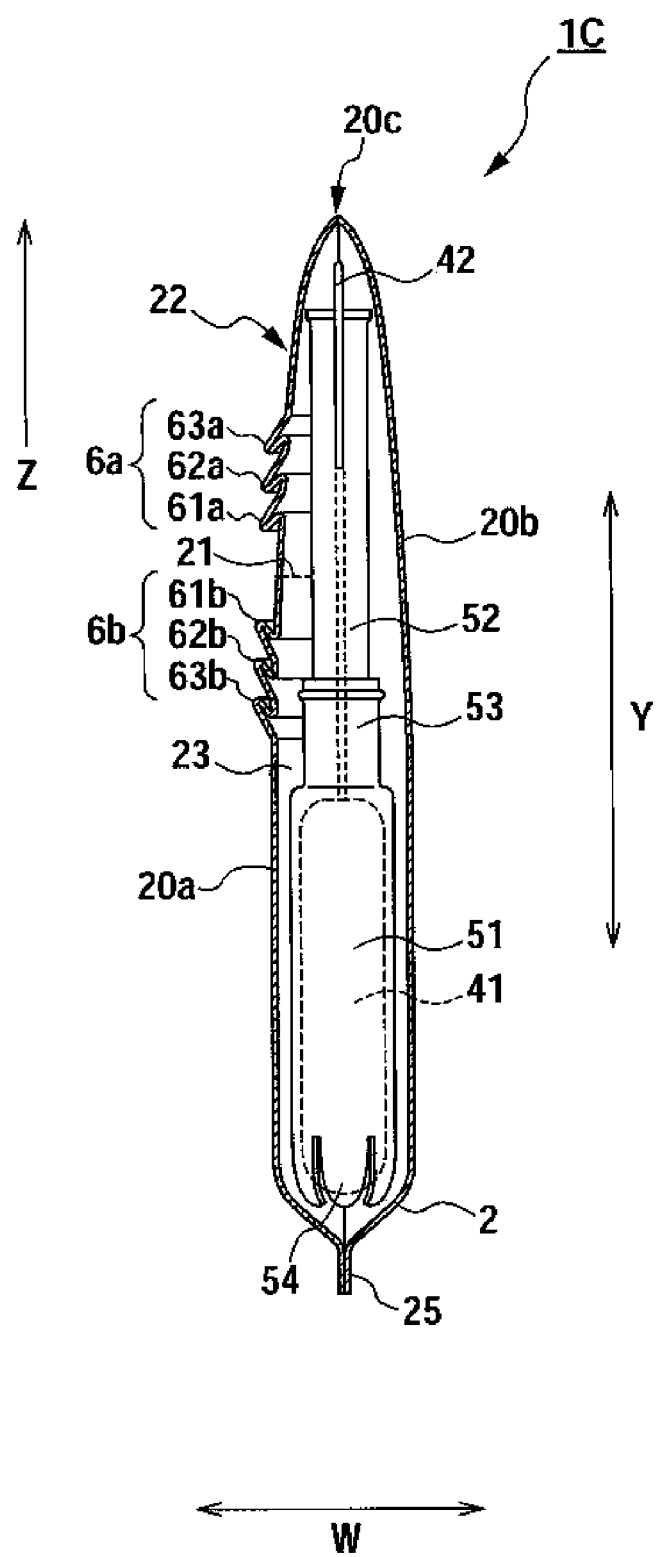
FIG. 6 is a schematic view showing a cross-section taken along line C-C of the individual packaging body shown in FIG. 5.
Figure 7:
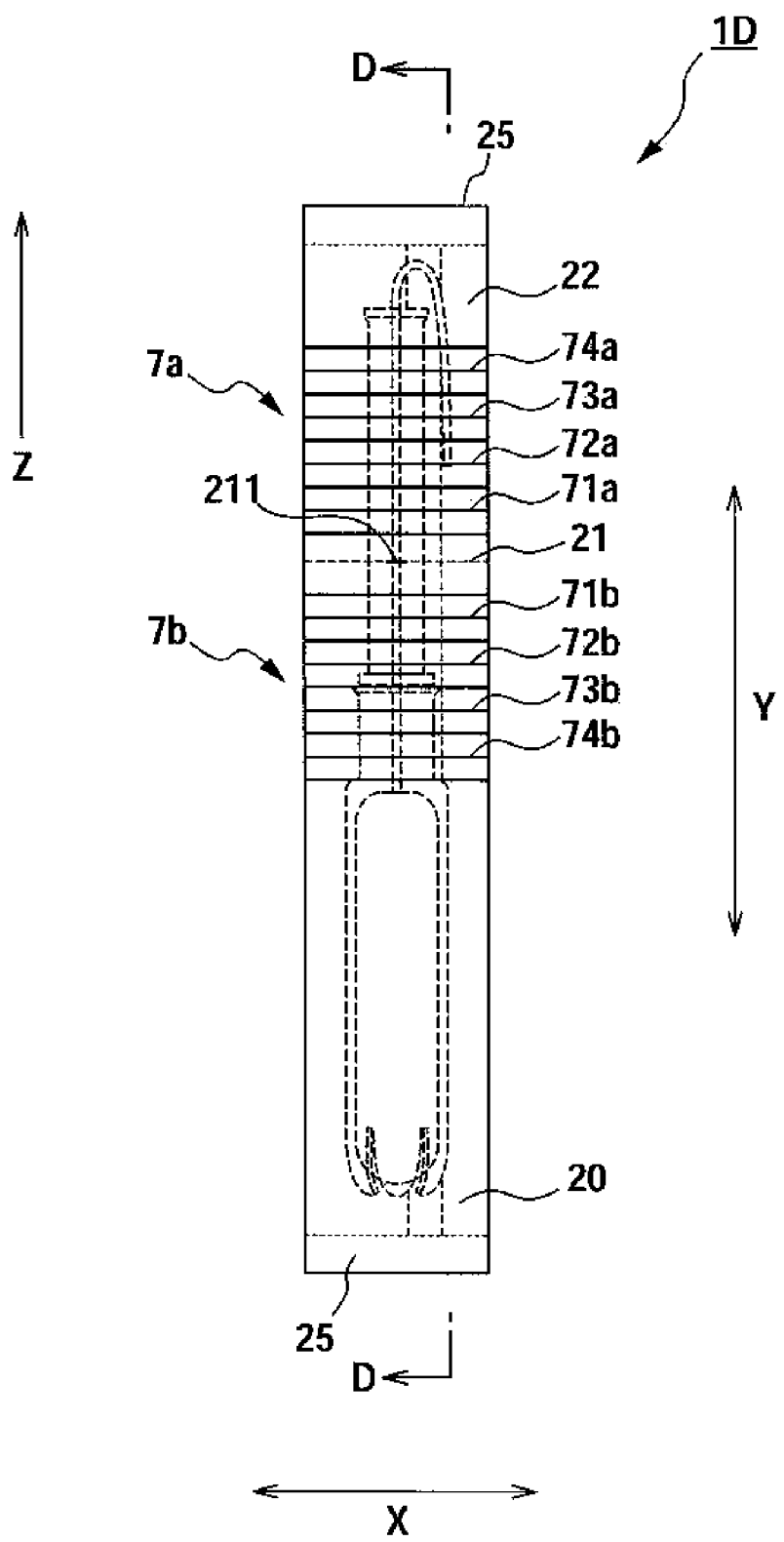
FIG. 7 is a front view of an individual packaging body according to a fourth embodiment of the present invention.
Figure 8:
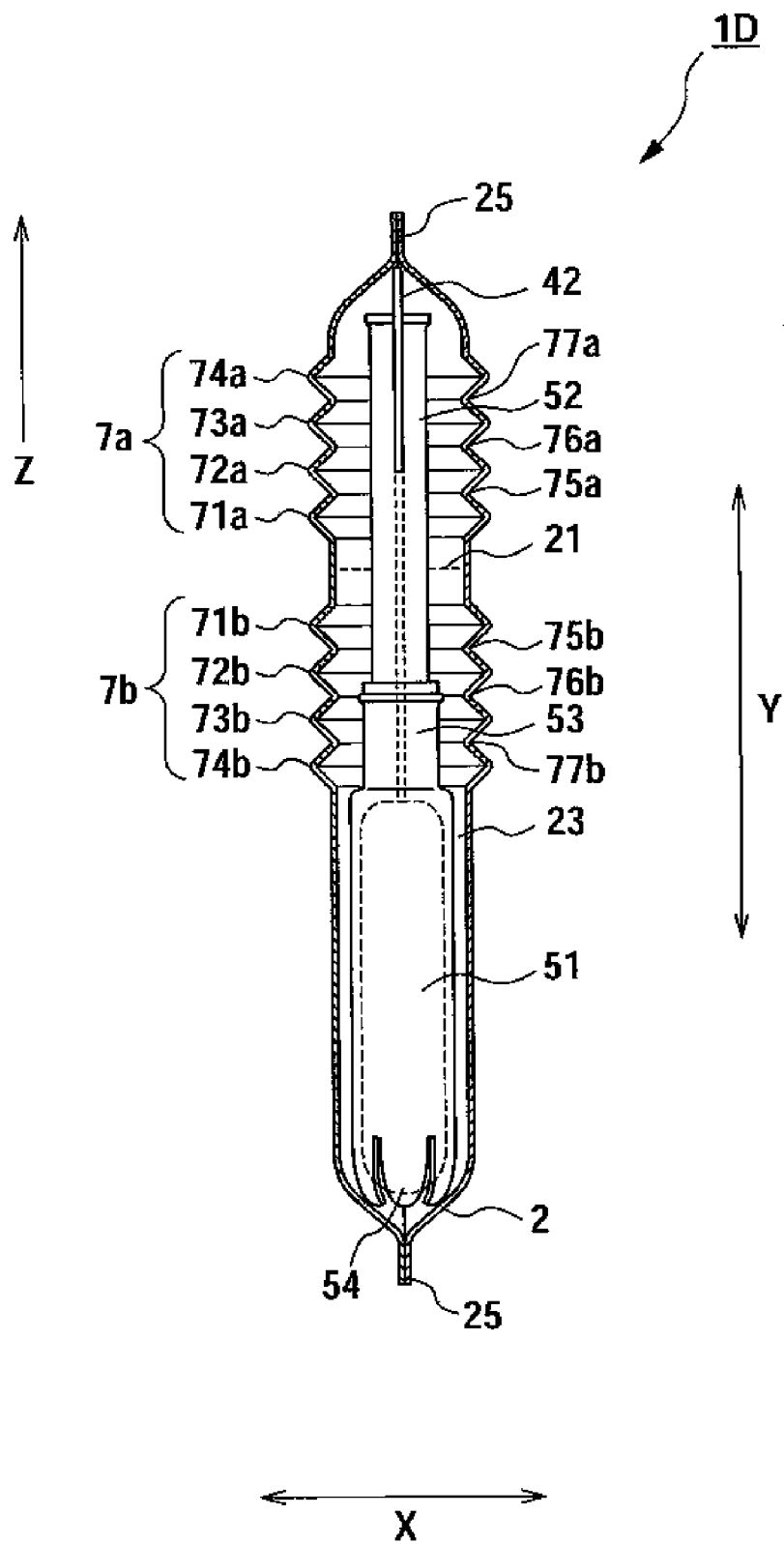
FIG. 8 is a schematic view showing a cross-section taken along line D-D of the individual packaging body shown in FIG. 7.
Figure 9:
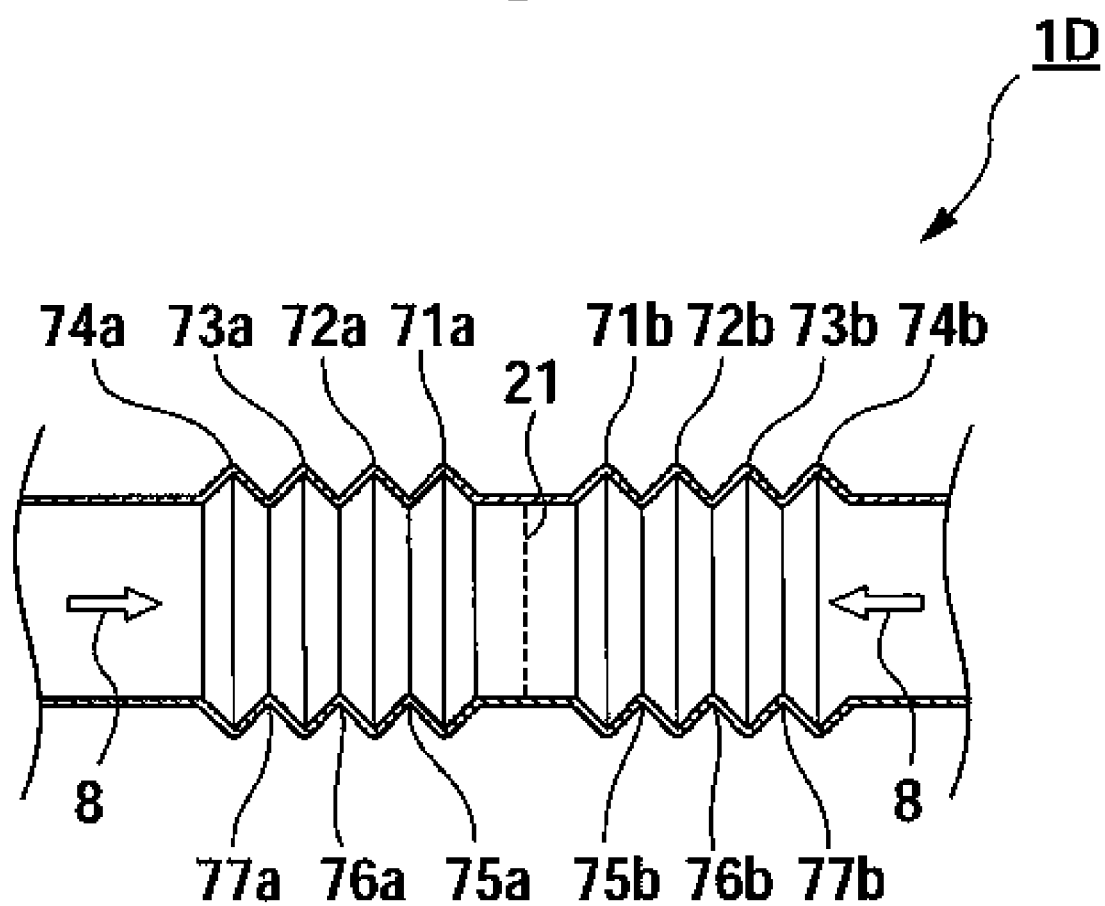
FIG. 9 is a partial enlarged view showing a lateral face of the individual packaging body shown in FIG. 7.
Figure 10:
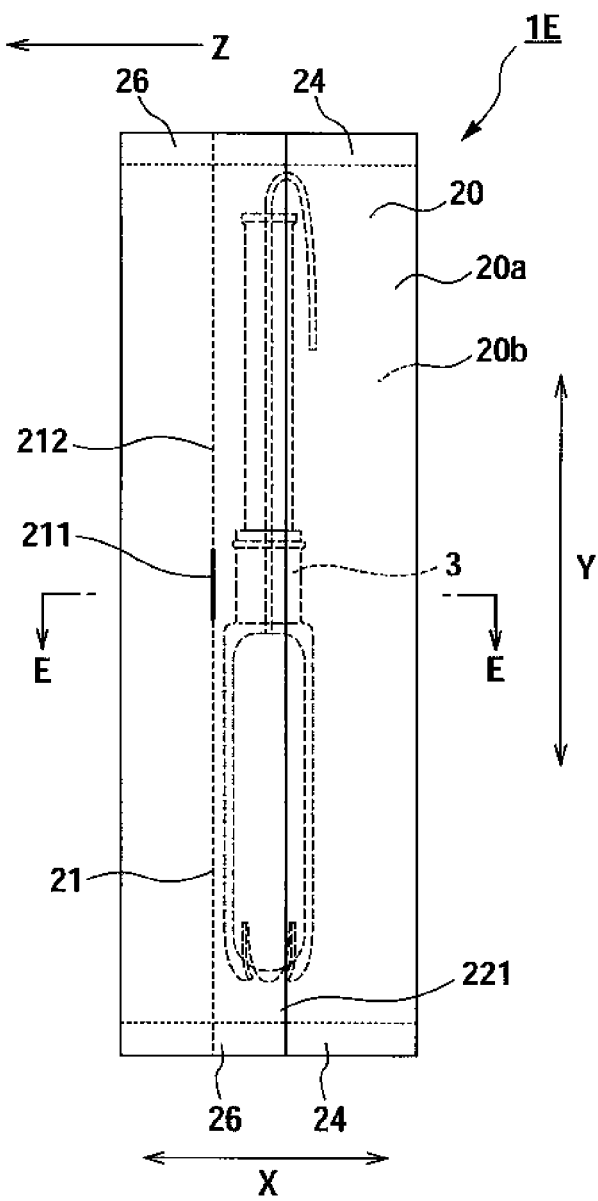
FIG. 10 is a front view of an individual packaging body according to a fifth embodiment of the present invention.
Figure 11:
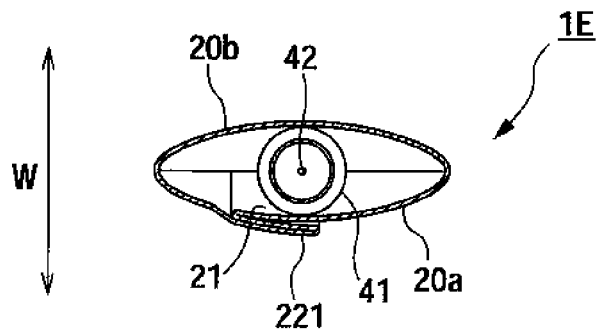
FIG. 11 is a schematic view showing a cross-section taken along line E-E of the individual packaging body shown in FIG. 10.
Figure 12:
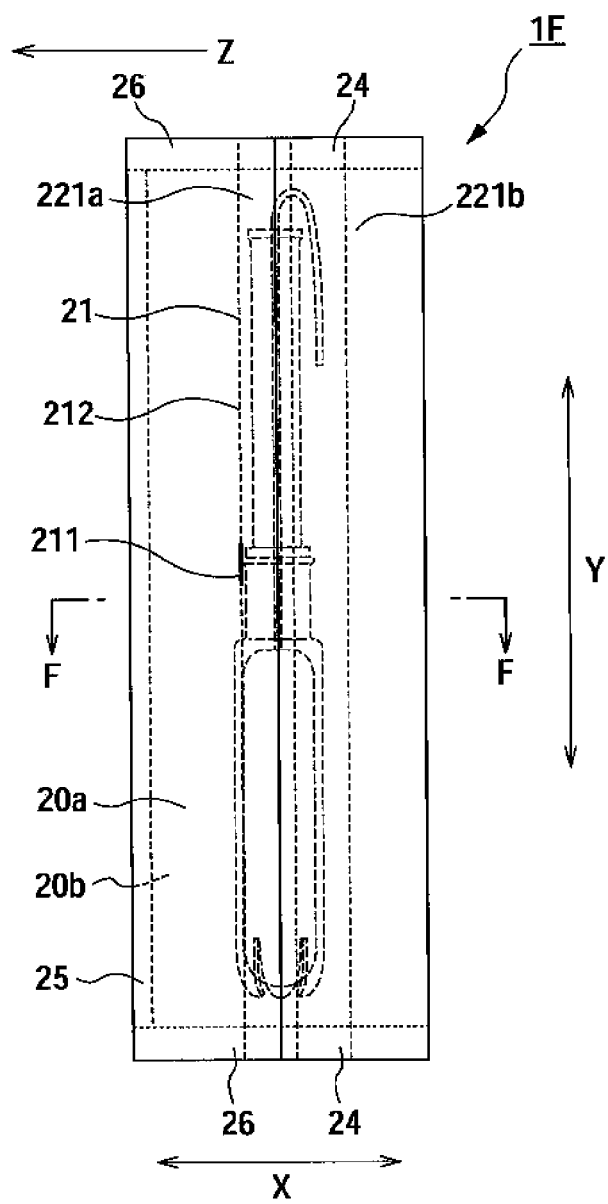
FIG. 12 is a front view of an individual packaging body according to a sixth embodiment of the present invention.
Figure 13:
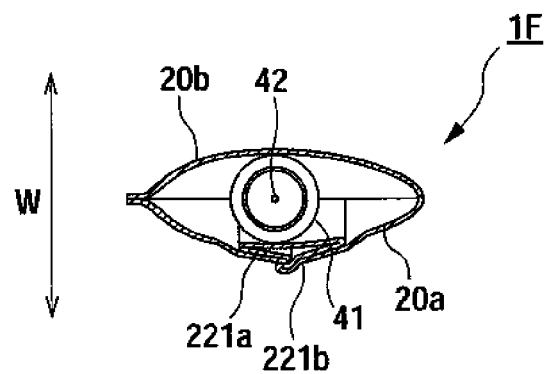
FIG. 13 is a schematic view showing a cross-section taken along line F-F of the individual packaging body shown in FIG. 12.
Figure 14A:
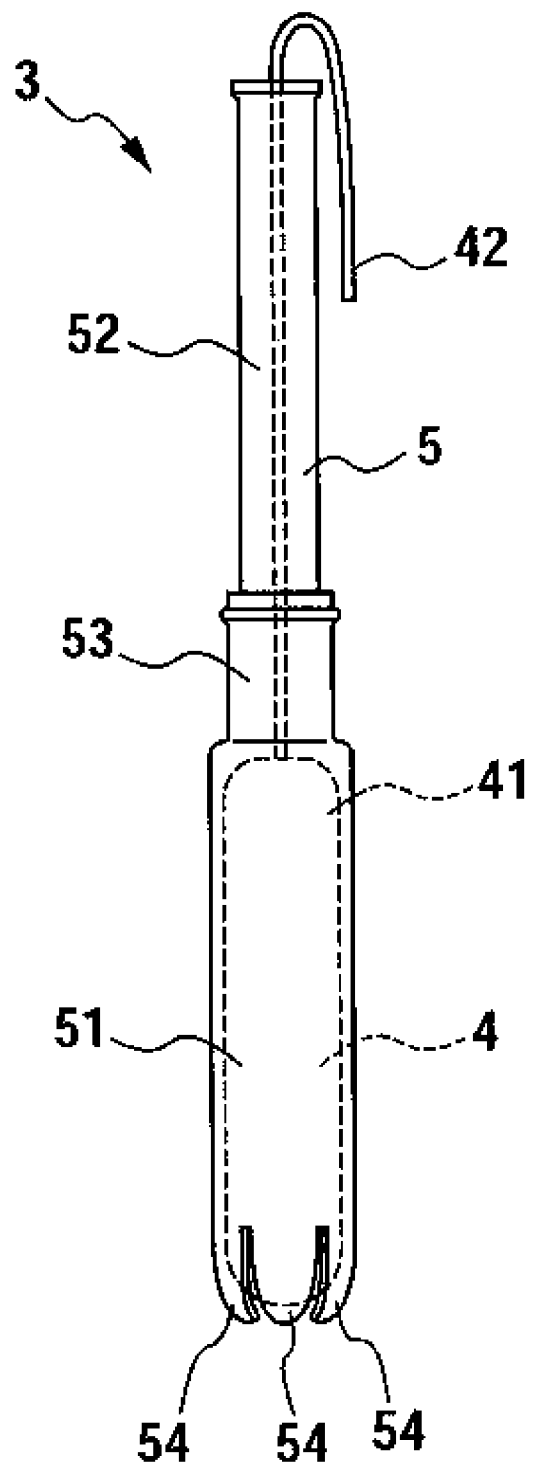
FIG. 14A shows a tampon with an applicator according to the present invention.
Figure 14B:
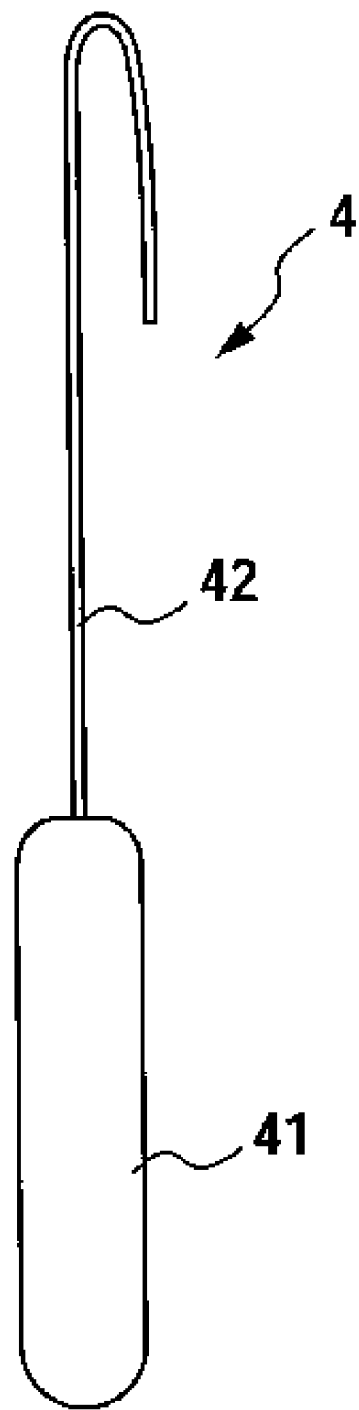
FIG. 14B shows a tampon main body according to the present invention.

FIG. 1 is a front view of an individual packaging body according to a first embodiment of the present invention. FIG. 2 is a schematic view showing a cross-section taken along line A-A of the individual packaging body shown in FIG. 1. FIG. 3 is a front view of an individual packaging body according to a second embodiment of the present invention. FIG. 4 is a schematic view showing a cross-section taken along line B-B of the individual packaging body shown in FIG. 3. FIG. 5 is a front view of an individual packaging body according to a third embodiment of the present invention. FIG. 6 is a schematic view showing a cross-section taken along line C-C of the individual packaging body shown in FIG. 5. FIG. 7 is a front view of an individual packaging body according to a fourth embodiment of the present invention. FIG. 8 is a schematic view showing a cross-section taken along line D-D of the individual packaging body shown in FIG. 7. FIG. 9 is a partial enlarged view showing a lateral face of the individual packaging body shown in FIG. 7. FIG. 10 is a front view of an individual packaging body according to a fifth embodiment of the present invention. FIG. 11 is a schematic view showing a cross-section taken along line E-E of the individual packaging body shown in FIG. 10. FIG. 12 is a front view of an individual packaging body according to a sixth embodiment of the present invention. FIG. 13 is a schematic view showing a cross-section taken along line F-F of the individual packaging body shown in FIG. 12. FIG. 14A shows a tampon with an applicator according to the present invention. FIG. 14B shows a tampon main body according to the present invention.

First Embodiment (1) Individual Packaging Body

As shown in FIGS. 1 and 2, an individual packaging body 1 according to a first embodiment is composed of a bag body 2 formed in a substantially flat bag shape and a tampon with an applicator 3, and the tampon with an applicator 3 is packed in a storage portion 23 formed in the bag body 2. The bag body 2 includes a tearing portion 21 that extends in a width direction X and is formed on a first face 20a, which is a face described later, and a lid portion 22 that separates in a direction orthogonal to the width direction X. A slack portion 221, which is a buffering structure portion formed so as to cover the tearing portion 21, is further provided in the lid portion 22. The tampon with an applicator 3 and the bag body 2 configuring the individual packaging body 1 are described hereinafter.

(2) Tampon with Applicator

As shown in FIG. 14A, the tampon with an applicator 3 includes a tampon main body 4 and an applicator 5 that is an insertion device.

(2-1) Applicator

The applicator 5 is formed of a synthetic resin material and includes an outer cylinder 51 in which the tampon main body 4 is housed and an inner cylinder that is slidably provided inside the outer cylinder 51 and formed so as to be capable of pushing out an absorbent core 41 of the tampon main body 4 housed in the outer cylinder 51. The outer cylinder 51 is provided with a grip portion 53 that can be gripped by a user in an end portion on a side on which the inner cylinder 52 is inserted. In addition, in an apex portion on an opposite side to the side on which the grip portion 53 is provided, a plurality of petals 54, which are separated from each other, is integrally formed. The absorbent core 41 pushed by the inner cylinder 52 is pushed out from between the petals 54 and ejected.

(2-2) Tampon Main Body

As shown in FIG. 14B, the tampon main body 4 includes the absorbent core 41 and a removal cord 42 that extends from a rear end portion of the absorbent core 41. In addition, the absorbent core 41 of the tampon main body 4 is housed inside the outer cylinder 51 and the removal cord 42 extending from the rear end portion of the absorbent core 41 extends through the outer cylinder 51 and the inner cylinder 52 toward a rear side of the inner cylinder 52.

The absorbent core 41 is formed by, for example, compressing hydrophilic fiber such as cotton, rayon and the like, and used in a state of being wrapped by a liquid permeable sheet such as non-woven fabric. The removal cord 42 is sewn onto the liquid permeable sheet in order to be joined with the absorbent core 41.

(2-3) Mode of Usage

In order to use the tampon with an applicator 3, a user first grips the grip portion 53 provided on the outer cylinder 51 and inserts the outer cylinder 51 of the applicator 5 into a vaginal cavity. Thereafter, the user pushes the inner cylinder 52 into the outer cylinder 51 while gripping the grip portion 53. As a result, the absorbent core 41 housed in the outer cylinder 51 is pushed out by the inner cylinder 52 and the petals 54 in the apex portion of the outer cylinder 51 are deformed to open. The absorbent core 41 is thus inserted into the vagina. The absorbent core 41 inserted into the vaginal cavity of a woman during menstruation absorbs body fluid such as menstrual blood. In addition, the removal string 42 is left outside of the vaginal cavity while the absorbent core 41 is inserted into the vaginal cavity. The absorbent core 41 can be removed from the vagina after use by pulling the removal string 42.

(3-1) Bag Body

The bag body 2 is formed of a substantially long sheet-like member. More specifically, the bag body 2 is formed in a bag shape by folding the sheet-like member at a first folding portion 20c and joining both sides in the width direction X (side-sealed portions 24, 24) of each of the first face 20a and a second face 20b, which are formed by folding. In addition, the bag body 2 is made into a flat-shaped individual packaging body 1 by enclosing the tampon with an applicator 3 and then joining an insertion opening for the tampon with an applicator on an opposite side to the first folding portion 20c in a longitudinal direction Y (bottom-sealed portion 25).

In the bag body 2 formed in a bag shape by joining the side-sealed portions 24, 24, a housing portion 23 for housing the tampon with an applicator 3 is formed in a portion not being joined between the first face 20a and the second face 20b. The housing portion 23 houses the tampon with an applicator 3 by opening the portion not being joined in the bag body 2.

Here, as a length in the longitudinal direction Y of the bag body 2 in the first embodiment, a length in a range of a total length of the applicator 5 in a state of housing the absorbent core 41 plus 10 to 40 mm can be exemplified.

Meanwhile, as a length in the width direction X of the bag body 2 in the first embodiment, a length in a range of 180 to 320% of the external diameter of the outer cylinder 51 of the applicator 5 can be exemplified. Preferably, a length in a range of 180 to 270% of the external diameter of the outer cylinder 51 of the applicator 5 can be exemplified.

In addition, as the length in the longitudinal direction Y of the bag body 2 in the first embodiment, a length in a range of a length of the outer cylinder 51 of the applicator 5 to a total length of the applicator 5 in a state of housing the absorbent core 41 plus 10 mm can be exemplified. It should be noted that the housing portion 23 is a portion for housing the tampon with an applicator 3 in the bag body 2, for example, a portion formed in a bag shape from the tearing portion 21 to the bottom-sealed portion 25.

Furthermore, as a width of the side-sealed portions 24, 24 for joining both side portions in the longitudinal direction Y of the bag body 2 in the first embodiment, a width in a range of 3 to 6 mm can be exemplified.

The tearing portion 21 extending in the width direction X is provided in the first face 20a of the bag body 2 of the individual packaging body 1. The tearing portion 21 is formed in a convex shape in a tearing direction Z and in a mountain shape with a substantially central portion, which is an apex thereof, being flat (parallel in the width direction X). In addition, the tearing portion 21 is formed by providing a plurality of slits intermittently in the width direction X of the bag body 2. In other words, in the tearing portion 21, slits are formed in a shape of a so-called perforated line in the width direction X of the bag body 2.

The tearing portion 21 includes a first slit portion 211 provided in a substantially central portion and a second slit portion 212 provided on both sides of the first slit portion 211, a slit length of the first slit portion 211 being greater than that of the second slit portion 212. By thus providing the first slit portion 211 having a greater slit length in the substantially central portion, the tearing portion 21 becomes easier to be torn in a case of opening thereof.

In addition, the tearing portion 21 is formed in the individual packaging body 1 after packing the abovementioned tampon with an applicator 3, in a portion corresponding to the inner cylinder 52 of the applicator 5 being packed therein. It should be noted that the tearing portion 21 is only required to be formed at a position allowing a user to pick up the inner cylinder 52 in the individual packaging body 1 after that the bag body 2 is opened.

In a lid portion 22, a slack portion 221, which is a buffering structure portion formed so as to cover the tearing portion 21, is formed. The slack portion 221 is formed by slackening a portion of the bag body 2 in the lid portion 22. More specifically, the slack portion 221 is formed by folding the lid portion 22 at a second folding portion 223 with a surface side facing inside, and then folding at a third folding portion 224 with the surface side facing outside. In other words, the second folding portion 223 constitutes an end portion of the slack portion 221 in the longitudinal direction Y and the third folding portion 224 constitutes a base portion of the slack portion 221. The slack portion 221 thus formed covers the tearing portion 21 and the sheet-like member is laminated by being thus folded.

Here, a length in the longitudinal direction Y of the slack portion 221 of the bag body 2 in the first embodiment can be any length allowing picking up thereof, for example at least 5 mm. Preferably, the length is in a range of 10 to 30 mm.

Then, the lid portion 22 of the bag body 2 is joined in a state of forming the slack portion 221 at the lid portion-sealed portions 26, 26 on both sides thereof. In other words, the slack portion 221 is also joined at both sides thereof and not joined in other portions. As a result, in the slack portion 221, a non-joined sheet-like member in a laminated portion formed by folding is partially slidable in the longitudinal direction Y. In such a configuration, the slack portion 221 can act as the buffering structure portion.

It should be noted that the lid portion-sealed portions 26, 26 are joined with a lower peel strength than in the side-sealed portions 24, 24 and the bottom-sealed portion 25. In other words, the lid portion-sealed portions 26, 26 are joined to such a degree that the lid portion 22 and the slack portion 221 can be separated from the first face 20a and the second face 20b.

The side-sealed portions 24, 24 and the bottom-sealed portion 25 are joined by heat sealing. The heat sealing is preferably performed under a sealing temperature of 80° C. to 110° C. and a pressure of 15 kgf/cm$^2$ to 30 kgf/cm$^2$. In addition, the lid portion-sealed portions 26, 26 are also joined by heat sealing, for example, in a case where the sheet-like member is a polyethylene resin film, under a sealing temperature of 90° C. to 120° C. and a linear pressure of 20 kgf/cm to 65 kgf/cm. It should be noted that the heat sealing is preferably performed in a predetermined embossing pattern.

A bonded area ratio of the side-sealed portions 24, 24 is preferably higher than that of the lid portion-sealed portions 26, 26. For example, the bonded area ratio of the side-sealed portion 24 is 36% while the bonded area ratio of the lid portion-sealed portion 26 is 27%.

(3-2) Constituent Material

A polyethylene film with fine convex portions provided on one side by embossing processing is used as a material for the sheet-shaped member. By providing the convex portions on an inner face of the bag body 2, it becomes difficult for the film to stick to each other and easier to handle. Any material that is suitable for individually packing a sanitary tampon can be used as the sheet-shaped member without particular limitation. For example, a soft film such as a polyethylene film and a polypropylene film, spun-bonded nonwoven fabric, SMS (spun-bonded/melt-blown/spun-bonded) nonwoven fabric, a sheet material obtained by laminate coating one side of a nonwoven fabric or paper with a polyethylene resin layer, a laminated body obtained by applying an adhesive on a nonwoven fabric or paper and laminating a polyethylene film thereon, and the like can be exemplified. The soft film such as a polyethylene film and a polypropylene film, which has a heat-sealing property, can be easily joined and thus is particularly preferable.

In addition, these can be single layered or multi-layered. Furthermore, these can be used singly or in combination.

(4) Operation and Effect

As described above, in the individual packaging body 1 according to the present embodiment, in a case where a force, which is different than that intended by the user, to open the individual packaging body 1 (a force to open the tearing portion 21 formed on the first face 20a) is applied between the end portion of the individual packaging body 1 and the tearing portion 21 (in the vicinity of the end portion on a side in the tearing direction Z) in a tearing direction Z, for example, a non-joined laminated portion in the slack portion 221 provided in the vicinity of the tearing portion 21 is slidingly moved in the tearing direction. By thus slidingly moving the non-joined portion in the slack portion 221 in the tearing direction Z, the force to open can be dispersed. In other words, the force can be buffered. This can inhibit a force being transferred to the tearing portion.

In addition, in a case of opening the tearing portion 21, a user grips the non-joined portion of the slack portion 221 with fingers, thereby restricting a sliding movement of the non-joined portion of the slack portion 221 in the tearing direction Z. As a result, when a user intends to open the tearing portion 21, a force is transferred directly to the tearing portion 21 and the tearing portion 21 can be easily torn. In this case, the slack portion 221 functions as a knob portion for opening when a user intends to open the tearing portion 21.

As described above, even in a case where the individual packaging body 1 is carried in a bag, a pouch and the like, direct transfer of force to the tearing portion 21 can be inhibited and accidental opening of the tearing portion 21 can be prevented by providing the slack portion 221.

In addition, by providing the slack portion 221, a user can easily find the tearing portion 21 and the convenience of the individual packaging body 1 is improved. Alternatively, a guiding sign that indicates the position of the tearing portion can be provided in the vicinity of the slack portion 221.

In addition, even in a case where the lid portion-sealed portion 26 is peeled off by pinching and pulling the slack portion 221 in the tearing direction Z, the side-sealed portions 24, 24 on a side to the housing portion 23 will not be peeled off since the tearing portion 21 is provided on a border between the base portion of the slack portion 221 and the housing portion 23.

Moreover, the tearing portion 21 can be made easy to open by providing a plurality of intermittent slits, and even easier to open by making a length of the slits formed in a substantially central portion of the bag body in the width direction X longer than that of the slits formed on both sides thereof in the width direction X.

Furthermore, since the tearing portion 21 is formed in a position corresponding to the inner cylinder 52 of the applicator 5 being packed, a user can easily pinch the inner cylinder 52 and easily pick up the tampon with an applicator 3 after opening the individual packaging body 1.

In addition, by providing a lid portion 22, even in a case where a user must carry the applicator 5 after use, the user can carry the applicator 5 without soiling other objects by putting the applicator 5 in the housing portion 23 of the bag body 2 and closing the lid of.

Furthermore, the tearing portion is not separated off since the lid portion 22 is formed integrally with the housing portion 23, thereby avoiding further generation of trash and the like.

Moreover, by covering the tearing portion 21 with the slack portion 221, the tearing portion 21 is not exposed. Therefore, even in a case where a slit for opening is formed in the tearing portion 21, intrusion of dust and bacteria through the slit can be inhibited.

Likewise, by packing the cylindrically shaped tampon with an applicator 3 in the flat bag body 2, the individual packaging body 1 becomes solid and easier to open the tearing portion 21, in other words easier for a user to open from the tearing portion 21.

(5) Alternatives

It should be noted that, in the present embodiment, the bag body 2 is formed by folding a piece of a sheet-like member into two; however, the present invention is not limited thereto. For example, the bag body 2 can be formed by laminating two pieces of a sheet-like member.

In addition, in the present embodiment, the tearing portion 21 is formed in a mountain shape with a flat apex by a straight slit traversing in the width direction X of the bag body 2; however, the present invention is not limited thereto. The tearing portion 21 can be formed in a curve or with a combination of a straight line and a curve. For example, the tearing portion 21 can be formed in a wave shape, an arc, a V shape and the like.

In addition, in the present embodiment, the tearing portion 21 is configured with a plurality of slit portions that is formed intermittently in the width direction X; however, the present invention is not limited thereto. The tearing portion 21 is required to be configured to be separable at a predetermined position on a bag body 2. For example, a predetermined position of the bag body 2 can be made separable by making the position thin-walled.

It should be noted that, the individual packaging body 1 according to the first embodiment can be applied to a case where extra space in the bag body 2 is small with respect to the tampon with an applicator 3 or a case where the sheet-like member is low in strength. This is because, for example, in case where an extra space in the bag body 2 is small with respect to the tampon with an applicator 3 or in a case where the sheet-like member is low in strength, a property for dispersing a force applied in the tearing direction Z is insufficient and accidental opening is likely to happen.

Other Embodiments

Second to sixth embodiments of the present invention are described with reference to FIGS. 3 to 13. The second embodiment shows another embodiment where a pair of slack portions is provided. The third embodiment shows another embodiment where a pair of buffering portions, which are other buffering structure portions, is provided. The fourth embodiment shows another embodiment where a pair of accordion portions is provided on a bag body formed in a cylindrical shape. The fifth embodiment shows another embodiment where the tearing portion is provided in the longitudinal direction Y. The sixth embodiment shows another embodiment where the tearing portion is provided in the longitudinal direction and a pair of slack portions is provided.

In the following description, the same reference numerals have been retained for similar parts that are identical to that described in the first embodiment, with the descriptions thereof omitted.

Second Embodiment

An individual packaging body 1B according to the second embodiment is similar to the individual packaging body 1 in the first embodiment. The individual packaging body 1B of the second embodiment is described hereinafter focusing on differences from the individual packaging body 1 in the first embodiment.

As shown in FIGS. 3 and 4, the individual package 1B according to the second embodiment includes a first slack portion 221a and a second slack portion 221b. The first slack portion 221a and the second slack portion 221b are similarly configured to the slack portion 221 in the first embodiment. In addition, the first slack portion 221a is formed on a side of the tearing portion 21 to the tearing direction Z and the second slack portion 221b is formed on a side of the tearing portion 21 opposite to the tearing direction Z. Furthermore, the first slack portion 221a is provided so as to cover the first slit portion 211 that is provided in a substantially central portion of the tearing portion 21 and the second slack portion 221b is provided so as to cover the third folding portion 223a of the first slack portion 221a.

The first slack portion 221a and the second slack portion 221b are both disposed along the first face 20a on a surface side of the first face 20a.

As a result, the individual packaging body 1B according to the second embodiment provides the following effects in addition to the effects of the individual packaging body 1 according to the first embodiment.

By providing the first slack portion 221a and the second slack portion 221b, which are formed by folding the sheet-like member and without joining faces overlapping each other, on sides of the tearing portion 21 in the tearing direction Z and in an opposite direction thereto, the individual packaging body 1B according to the second embodiment can, for example, disperse a force applied in the tearing direction Z intended to open the tearing portion 21 by slidingly moving (deforming) a portion of the first and the second slack portions 221a and 221b. Direct transfer of force to the tearing portion 21 can be thus inhibited by buffering a force in the tearing direction. This can prevent accidental opening of the tearing portion 21. In addition, unlike the first embodiment, by providing the first slack portion 221a and the second slack portion 221b across the tearing portion 21 on a side of the tearing portion 21 in the tearing direction Z and on a side thereof in an opposite direction thereto, more force can be dispersed and direct transfer of force to the tearing portion 21 can be further inhibited.

In this embodiment, the first slack portion 221a and the second slack portion 221b are disposed so that at least a portion thereof overlaps each other; however, the present invention is not limited thereto. For example, the first slack portion 221a and the second slack portion 221b can be disposed so as not to overlap each other.

In addition, in the present embodiment, the first slack portion 221a is disposed on a surface side of the first face 20a and the second slack portion 221b is disposed so as to overlap the first slack portion 221a; however, the present invention is not limited thereto. For example, the second slack portion 221b can be disposed on the surface side of the first face 20a and the first slack portion 221a can be disposed so as to overlap the second slack portion 221b.

In addition, in the present embodiment, the tearing portion 21 is formed in a mountain shape so as to be convex in the tearing direction Z, and a portion of the tearing portion 21 in the tearing direction Z is formed to be covered with the first slack portion 221a; however, the present invention is not limited thereto. For example, regardless of a shape of the tearing direction 21, the whole tearing portion 21 can be formed so as to be covered with the first slack portion 221a or with the second slack portion 221b.

Third Embodiment

An individual packaging body 1C according to the third embodiment is similar to the individual packaging body 1 in the first embodiment and the individual packaging body 1B in the second embodiment. The individual packaging body 1C of the third embodiment is described hereinafter focusing on a difference from the individual packaging body 1 in the first embodiment and the individual packaging body 1B in the second embodiment.

As shown in FIGS. 5 and 6, the individual packaging body 1C shown in the third embodiment includes a first buffering portion 6a that is a buffering structure portion provided on a side of the tearing portion 21 in the tearing direction Z and a second buffering portion 6b that is a buffering structure portion provided on a side of the tearing portion 21 in an opposite direction to the tearing direction Z.

The first buffering portion 6a is provided on a side to the first face 20a and composed of a plurality of slack portions that is small in depth and continuously formed. In addition, the first buffering portion 6a is formed so that a slack portion is disposed on a side to the tearing portion 21. More specifically, in the first buffering portion 6a, a plurality of slack portions 61a, 62a, and 63a formed by folding a portion of the first face 20a in the lid portion 22 of the bag body 2 so that peaks and valleys continue alternately is provided.

Similarly, the second buffering portion 6b is provided on a side to the first face 20a and composed of a plurality of small slack portions that is continuously formed so as to face the first buffering portion across the tearing portion 21. In addition, the second buffering portion 6b is formed so that a slack portion is disposed on a side to the tearing portion 21. More specifically, in the second buffering portion 6b, a plurality of slack portions 61b, 62b, and 63b formed by folding a portion of the first face 20a in the lid portion 22 of the bag body 2 is provided.

In such a configuration, when a force intended to open the tearing portion 21 is applied in the tearing direction Z at any position on the first face 20a between the first buffering portion 6a and an end portion of the bag body 2 in the tearing direction Z (hereinafter referred to as predetermined position), the plurality of slack portions 61a, 62a, and 63a are each slidingly moved. More specifically, a non-joined laminated portion of each of the slack portions 61a, 62a, and 63a is slidingly moved. Transfer of a force that is applied at the predetermined position in the tearing direction Z to the tearing portion 21 can be thus inhibited. In other words, the first buffering portion 6a acts as a buffering structure portion. Similarly, the second buffering portion 6b also acts as the buffering structure portion since each of the plurality of slack portions 61b, 62b, and 63b is slidingly moved.

It should be noted that, a length in the range of 3 mm to 30 mm can be exemplified as a length of the first buffering portion 6a and the second buffering portion 6b before slidingly moving. The length can be any length, for example, that allows for pinching.

In addition, a length of the first buffering portion 6a and the second buffering portion 6b being extended in the extending direction is preferably at least 130% of the length thereof not being extended. This is because, by making the first buffering portion 6a and the second buffering portion 6b extensible to at least 130%, direct force applied in the tearing direction Z can be further buffered.

As described above, the individual packaging body 1C is different from the first embodiment and the second embodiment in that the first buffering portion 6a including the plurality of slack portions 61a, 62a, and 63a is provided on a side of the tearing portion 21 in the tearing direction Z and the second buffering portion 6b including the plurality of slack portions 61b, 62b, and 63b is provided on a side of the tearing portion 21 in an opposite direction to the tearing direction Z. In this way, for example, in a case where a direct force for opening the tearing portion 21 is applied in the tearing direction Z, more force can be buffered by providing the plurality of slack portions 61a, 62a, 63a, 61b, 62b, and 63b.

Additionally, the individual packaging body 1C according to the third embodiment provides the following effects in addition to the effects of the individual packaging bodies 1 and 1B according to the first and the second embodiments.

In the individual packaging body 1C, the slack portions 61a, 62a, and 63a of the first buffering portion 6a and the slack portions 61b, 62b, and 63b of the second buffering portion 6b are formed to be small in depth. In opening the tearing portion 21, a user pinches the first buffering portion 6a and the second buffering portion 6b respectively and opens the tearing portion 21 while limiting extension of the slack portions. In this case, since the plurality of slack portions 61a, 62a, 63a, 61b, 62b, and 63b being small in depth is provided, the slack portions hook on to fingers by frictional force when being pinched and make it easier to pull in the tearing direction.

In the present embodiment, the first buffering portion 6a is provided on a side of the tearing portion 21 in the tearing direction Z and the second buffering portion 6b is provided on a side of the tearing portion 21 in an opposite direction to the tearing direction Z as the buffering structure portion; however, the present invention is not limited thereto. For example, the first buffering portion 6a or the second buffering portion 6b can be provided on any one of a side of the tearing portion 21 in the tearing direction Z and a side of the tearing portion 21 in an opposite direction to the tearing direction Z.

Furthermore, in the present embodiment, one first buffering portion 6a is provided on a side of the tearing portion 21 in the tearing direction Z and one second buffering portion 6b is provided on a side in an opposite direction to the tearing direction Z; however, the present invention is not limited thereto. For example, a plurality of first buffering portions 6a can be provided on a side of the tearing portion 21 in the tearing direction Z and a plurality of second buffering portions 6b can be provided on a side in an opposite direction to the tearing direction Z.

In addition, the present embodiment is configured to be extensible in the tearing direction Z by providing a plurality of slack portions that is small in depth; however, the present invention is not limited thereto. For example, the present embodiment can be formed to be extensible by a shaping process or by using a stretchable material in the first buffering portion 6a and the second buffering portion 6b.

Fourth Embodiment

An individual packaging body 1D according to the fourth embodiment is similar to the individual packaging 1 in the first embodiment. The individual package 1D of the fourth embodiment is described hereinafter focusing on a difference from the individual packaging body 1 in the first embodiment.

As shown in FIGS. 7 to 9, the individual packaging body 1D shown in the fourth embodiment includes a first accordion portion 7a that is a buffering structure portion provided on a side of the tearing portion 21 in the tearing direction Z and a second accordion portion 7b that is a buffering structure portion provided on a side of the tearing portion 21 in an opposite direction to the tearing direction Z.

The individual packaging portion 1D is formed in a substantially cylindrical shape by joining both end portions in the longitudinal direction Y to be sealed. The first accordion portion 7a and the second accordion portion 7b are formed on a peripheral surface of the individual packaging portion 1D.

The first accordion portion 7a is formed by folding the sheet-shaped member so that a plurality of peak portions 71a, 72a, 73a, and 74a and a plurality of valley portions 75a, 76a, and 77a alternately continue. Similarly, the second accordion portion 7b is formed by folding the sheet-shaped member so that a plurality of peak portions 71b, 72b, 73b, and 74b and a plurality of valley portions 75b, 76b, and 77b are continuous alternately.

In such a configuration, in a case where a force intended to open the tearing portion 21 is applied in the tearing direction Z at a predetermined position on the first surface 20a between the first accordion portion 7a and an end portion of the bag body 2 in the tearing direction Z, the first accordion portion 7a deforms to extend. More specifically, by a force applied in the tearing direction Z, an angle of an apex of the plurality of peak portions 71a, 72a, 73a, and 74a provided in the first accordion portion 7a becomes larger and an interval between the valley portions 75a, 76a, and 77a becomes larger. The first accordion portion 7a is thus deformed to extend and the force applied at the predetermined position in the tearing direction Z is not transferred to the tearing portion 21. In other words, the first accordion portion 7a acts as the buffering structure portion.

Similarly, the second accordion portion 7b is also deformed to extend such that an angle of an apex of the plurality of peak portions 71b, 72b, 73b, and 74b provided in the second accordion portion 7b becomes larger and an interval between the valley portions 75b, 76b, and 77b becomes larger. In other words, the second accordion portion 7b acts as the buffering structure portion.

A length in the range of 3 mm to 30 mm can be exemplified as a length in the extending direction of the first accordion portion 7a and the second accordion portion 7b not being extended. The length can be any length, for example, that allows for pinching.

In addition, a length of the first accordion portion 7a and the second accordion portion 7b being extended in the extending direction is preferably at least 130% of the length thereof not being extended. This is because, by making the first accordion portion 7a and the second accordion portion 7b extensible to at least 130%, direct force applied in the tearing direction Z can be further buffered.

Furthermore, as shown in FIG. 9, the individual packaging body 1D is provided with a guiding sign 8 that is a guiding element indicating a position of the tearing portion 21. More specifically, the guiding sign 8 is provided on the bag body 2 by printing an arrow, for example, in the vicinity of the first accordion portion 7a and the second accordion portion 7b. By thus providing the guiding sign 8 suggesting the position of the tearing portion 21, a user can reliably open and neatly tear the tearing portion 21, for example. Since a cut surface is thus neatly formed, for example, in a case of temporarily putting a used applicator or a used tampon main body in the bag body for discarding thereof, the used applicator or the used tampon can be easily put in the bag body without soiling thereof.

In addition, the individual packaging body 1D according to the fourth embodiment provides the following effects in addition to the effects of the individual packaging body 1 according to the first embodiment. In the individual packaging body 1D, the peak portions 71a, 72a, 73a and 74a of the first accordion portion 7a and the peak portions 71b, 72b, 73b and 74b of the second accordion portion 7b are not provided with a slack portion 221. In opening the tearing portion 21, a user pinches the first accordion portion 7a and the second accordion portion 7b respectively and opens the tearing portion 21 while limiting extension of the successive peak portions. In this case, since the peak portions are provided in the first and the second accordion portion 7a and 7b, the peak portions hook onto fingers by frictional force when being pinched and make it easier to pull in the tearing direction.

In the present embodiment, the first accordion portion 7a is provided on a side of the tearing portion 21 in the tearing direction Z and the second accordion portion 7b is provided on a side of the tearing portion 21 in an opposite direction to the tearing direction Z as the buffering structure portion; however, the present invention is not limited thereto. For example, the first accordion portion 7a or the second accordion portion 7b can be provided on any one of a side of the tearing portion 21 in the tearing direction Z and a side of the tearing portion 21 in an opposite direction to the tearing direction Z.

Furthermore, in the present embodiment, one first accordion portion 7a is provided on a side of the tearing portion 21 in the tearing direction Z and one second accordion portion 7b is provided on a side in an opposite direction to the tearing direction Z; however, the present invention is not limited thereto. For example, a plurality of first accordion portions 7a can be provided on a side of the tearing portion 21 in the tearing direction Z and a plurality of second accordion portions 7b can be provided on a side in an opposite direction to the tearing direction Z.

In addition, in the present embodiment, the first accordion portion 7a or the second accordion portion 7b is formed in a mountain shape in which a cross-section in the tearing direction Z has linear lateral face portions; however, the present invention is not limited thereto. For example, the lateral face portions of the cross-section can be curved lines, or one straight line and one curved line. Furthermore, a shape of the apex portion of the mountain shape is not limited to an acute convex shape and can also be a curved line (curved surface) or a flat surface. For example, a shape of a cross-section can be a trapezoidal shape, an omega shape, a wave-like shape and the like.

In addition, the first accordion portion 7a and the second accordion portion 7b of the present embodiment are each configured with four peak positions; however, the present invention is not limited thereto and, for example, can be configured with at least one peak portion.

In addition, in the present embodiment, a guiding element that indicates the position of the tearing portion 21 is provided as a guiding element; however, the present invention is not limited thereto. For example, the guiding element can indicate the tearing direction of the tearing portion 21 and, in a case where a grip portion that can be gripped with fingers such as the slack portion 221 is provided, the guiding element can indicate the position of the grip portion.

In addition, in the present embodiment, the guiding element is formed by printing an arrow indicating the position of the tearing portion 21; however, the present invention is not limited thereto. For example, the guiding element can be formed by printing a letter, a pattern, a figure and the like indicating the position or the tearing direction of the tearing portion 21.

Alternatively, the guiding element by tactile sensation can be formed by providing concavity and convexity by an embossing process or the like.

In addition, the present embodiment is configured to be extensible in the tearing direction by providing the peak portions and the valley portions alternatively; however, the present invention is not limited thereto. For example, the present embodiment can be formed to be extensible by a corrugating shaping process such as a gear process that forms a wave-like shape or by using a stretchable material in the first accordion portion 7a and the second accordion portion 7b.

Fifth Embodiment

An individual packaging body 1E according to the fifth embodiment is similar to the individual packaging body 1 in the first embodiment. The individual packaging body 1E of the fifth embodiment will be described hereinafter focusing on a difference from the individual packaging body 1 in the first embodiment.

As shown in FIGS. 10 and 11, in the individual packaging body 1E according to the fifth embodiment, the tearing portion 21 is formed along the longitudinal direction Y of the bag body 2. In addition, the slack portion 221 is formed in a tongue shape and provided along the longitudinal direction Y of the bag body 2. Furthermore, the lid portion 22 is formed along the longitudinal direction Y of the bag body 2 so as to be openable in the width direction X of the bag body 2.

The individual packaging body 1E is thus different from the first embodiment in that the slack portion 221 is formed along the longitudinal direction Y. In such a configuration, a non-joined portion in a surface facing the slack portion 221 is slidable in the width direction X. And, in the slack portion 221 formed along the longitudinal direction Y, a non-joined area becomes larger and a central portion in the longitudinal direction that is spaced apart from both end portions and joined with the first face 20a can further buffer a direct force applied in the tearing direction.

It should be noted that, the individual packaging body 1E according to the present embodiment is formed in a substantially cylindrical shape by heat-sealing a seal portion (not shown) extending in the longitudinal direction Y, and is formed in a bag shape by heat-sealing the side-sealed portion 24 and the lid portion-sealed portion 26 in both end portions of the bag body 2 in the longitudinal direction Y.

As described above, the individual packaging body 1E has the tearing portion 21 provided along the longitudinal direction Y of the bag body 2 so that the tearing direction is the width direction X, and provides the following effects in addition to the effects of the individual packaging body 1 according to the first embodiment.

In the individual packaging body 1E according to the fifth embodiment, a larger buffering portion can be provided by forming the slack portion 221 in a tongue shape in the width direction X of the bag body 2 and along the longitudinal direction Y, compared to a case where the slack portion 221 is provided along the width direction. X. In such a configuration, a portion movable in the tearing direction Z is also larger and a direct force applied in the tearing direction Z can thus be further buffered. In other words, a force applied to the tearing portion 21 in the tearing direction Z can be inhibited.

In addition, in the individual packaging body 1E according to the fifth embodiment, a larger tearing portion 21 can be provided by forming the tearing portion 21 along the longitudinal direction Y. As a result, for example, the tampon with an applicator 3 can be easily taken out and, in a case of temporarily putting a used applicator 5 or a used tampon main body 4 in the bag body 2 for discarding thereof, the used applicator 5 or the used tampon 4 can be easily put in the housing portion 23 of the bag body 2 through a large tearing portion 21.

In the present embodiment, the tearing portion 21 extending in the longitudinal direction Y is provided so as to extend over the whole bag body 2 along the longitudinal direction Y; however, the present invention is not limited thereto. For example, the tearing portion 21 may have a length openable to a length allowing the tampon with an applicator 3 packed in the individual packaging body 1E to be taken out. For example, the tearing portion 21 may have a length in a range of 25% to 70% of a length of the bag body 2 in the longitudinal direction. In this case, the first slot portion 211 can be formed in a substantial center of the tearing portion 21, for example, in the vicinity of a position to be pinched by a user in the slack portion 221.

It should be noted that, in the present embodiment, the tearing portion 21 is formed in a straight line; however, the present invention is not limited thereto. For example, the tearing portion 21 can be formed such as by a combination of a curved line and a straight line.

Sixth Embodiment

An individual packaging body 1F according to a sixth embodiment is similar to the individual packaging body 1E in the fifth embodiment. The individual packaging body 1F of the sixth embodiment is described hereinafter focusing on a difference from the individual packaging body 1E in the fifth embodiment.

As shown in FIGS. 12 and 13, the individual packaging body 1F of the sixth embodiment is different from the fifth embodiment in that a first slack portion 221a that is openable in the tearing direction Z and a second slack portion 221b that is openable in an opposite direction to the tearing direction Z are formed across the tearing portion 21.

The individual packaging body 1F provides the following effects in addition to the effects of the individual packaging body 1E according to the fifth embodiment. Namely, in the individual packaging body 1F according to the sixth embodiment, a larger buffering portion can be provided by providing the first slack portion 221a and the second slack portion 221b, compared to a case where the slack portion 221 is provided on one side of the tearing portion 21 along the longitudinal direction Y. In other words, a portion that can deform to extend in the tearing direction Z becomes larger and a force applied in the tearing direction Z can thus be further buffered. As a result, a force in the tearing direction applied to the tearing portion 21 can be further inhibited.

In the present embodiment, the tearing portion 21 extending in the longitudinal direction Y is provided so as to extend over the whole bag body 2 in the longitudinal direction Y; however, the present invention is not limited thereto. For example, the tearing portion 21 is required to have a length openable to a length allowing the tampon with an applicator 3 packed in the individual packaging body 1F to be taken out. For example, the tearing portion 21 is required to have a length in a range of 25% to 70% of a length of the bag body 2 in the longitudinal direction.

In addition, in the present embodiment, the first slack portion 221a and the second slack portion 221b are disposed so that at least a portion thereof overlaps each other; however, the present invention is not limited thereto. For example, the first slack portion 221a and the second slack portion 221b can be disposed so as not to overlap each other.

In addition, in the present embodiment, the first slack portion 221a is disposed on a surface side of the first face 20a and the second slack portion 221b is disposed so as to overlap the first slack portion 221a; however, the present invention is not limited thereto. For example, the second slack portion 221b can be disposed on the surface side of the first face 20a and the first slack portion 221a can be disposed so as to overlap the second slack portion 221b.

It should be noted that, although the tampon utilizes a tampon with an applicator 3 in the present invention, the present invention is not limited thereto. For example, the present invention can be applied to an individual packaging body that individually packs a tampon without an applicator.

The invention claimed is:

1. An individual packaging body for a tampon, having an elongated and flat bag body formed of a sheet-like member and a tampon with an applicator that is to be individually packed in the bag body, the individual packaging body comprising:
   a tearing portion having at least one slit portion that is formed continuously or intermittently in a width direction on the sheet-like member, said tearing portion having a convex shape with a central portion that is flat; and
   a buffering structure portion formed on at least one side in a tearing direction of the tearing portion on a first face of the bag body,
   wherein the buffering structure portion has a slack portion formed by slackening the sheet-like member,
   the tearing portion and the buffering structure portion extend in the same direction, and
   the slack portion covers the entire tearing portion.

2. The individual packaging body according to claim 1, wherein the slack portion has a side edge in a width direction of the bag body that is joined with the bag body.

3. The individual packaging body according to claim 1, wherein the buffering structure portion is formed on a first face of the flat bag body in a vicinity of the tearing portion, and the slack portion covers the entire tearing portion.

4. The individual packaging body according claim 1, wherein the buffering structure portion is formed by folding back the sheet-like member continuously so that peak portions and valley portions alternate continuously in the tearing direction.

5. The individual packaging body according to claim 1, wherein the buffering structure portion includes a first buffering structure portion and a second buffering structure portion extending parallel with each other, and the tearing portion is disposed in between the first and second buffering structure portions.

6. The individual packaging body according to claim 1, wherein the bag body includes a guiding element that indicates a position of the tearing portion or the tearing direction.

7. An individual packaging body for a tampon, having an elongated and flat bag body formed of a sheet-like member and a tampon with an applicator that is to be individually packed in the bag body, the individual packaging body comprising:
   a tearing portion having at least one slit portion that is formed continuously or intermittently in a width direction on the sheet-like member, said tearing portion having a convex shape with a central portion that is flat; and
   a buffering structure portion formed on at least one side in a tearing direction of the tearing portion,
   wherein the buffering structure portion has a slack portion formed by slackening the sheet-like member,
   wherein the bag body has first and second faces and the buffering structure portion is formed only on one of the first and second faces of the bag body.

* * * * *